(12) United States Patent
McEwen et al.

(10) Patent No.: US 11,219,464 B2
(45) Date of Patent: *Jan. 11, 2022

(54) METHOD AND APPARATUS FOR SHIELDING ENGAGEMENT OF A TOURNIQUET CUFF

(71) Applicant: Western Clinical Engineering Ltd., Vancouver (CA)

(72) Inventors: James A. McEwen, Vancouver (CA); Michael Jameson, North Vancouver (CA); Kenneth L. Glinz, Richmond (CA); Tom Yu Chia Lai, Vancouver (CA)

(73) Assignee: Western Clinical Engineering Ltd., Vancouver (CA)

( * ) Notice: Subject to any disclaimer, the term of this patent is extended or adjusted under 35 U.S.C. 154(b) by 434 days.

This patent is subject to a terminal disclaimer.

(21) Appl. No.: 15/860,586

(22) Filed: Jan. 2, 2018

(65) Prior Publication Data
US 2018/0140306 A1    May 24, 2018

Related U.S. Application Data

(63) Continuation of application No. 15/853,336, filed on Dec. 22, 2017, now abandoned, which is a
(Continued)

(51) Int. Cl.
*A61B 17/135* (2006.01)
(52) U.S. Cl.
CPC .................... *A61B 17/135* (2013.01)
(58) Field of Classification Search
CPC ..................................... A61B 17/135
See application file for complete search history.

(56) References Cited

U.S. PATENT DOCUMENTS

| 3,467,077 A | 9/1969 | Cohen |
| 3,552,383 A | 1/1971 | Krueger |

(Continued)

FOREIGN PATENT DOCUMENTS

| EP | 1996086 | 7/2017 |
| EP | 2496149 | 9/2017 |

OTHER PUBLICATIONS

International Search Report and Written Opinion for PCT/IB2018/053498, dated Aug. 13, 2018.
(Continued)

*Primary Examiner* — Katherine M Rodjom
(74) *Attorney, Agent, or Firm* — Klarquist Sparkman, LLP

(57) ABSTRACT

A low-cost contour cuff for surgical tourniquet systems comprises: a sheath containing an inflatable bladder, the sheath having an arcuate shape, an outer surface and a centerline equidistant between first and second side edges; a securing strap non-releasably attached to the outer surface and formed of substantially inextensible material having a shape that is predetermined and substantially flat, wherein the strap includes a bending portion near a first strap end and a fastening portion near a second strap end, and wherein the bending portion is adapted to allow twisting of the bending portion out of the substantially flat shape to facilitate positioning of the fastening portion into any of a plurality of positions in the substantially flat shape; and fastening means for releasably attaching the fastening portion of the securing strap to the outer surface whenever the sheath is curved into a position for surrounding a limb.

11 Claims, 3 Drawing Sheets

Related U.S. Application Data continuation-in-part of application No. 13/932,093, filed on Jul. 1, 2013, now abandoned, which is a continuation of application No. 12/828,078, filed on Jun. 30, 2010, now Pat. No. 8,480,842, which is a continuation of application No. 11/384,695, filed on Mar. 20, 2006, now Pat. No. 7,758,607.

(56) References Cited

U.S. PATENT DOCUMENTS

| | | | |
|---|---|---|---|
| 3,654,931 A * | 4/1972 | Hazlewood | A61B 17/135 606/202 |
| 3,892,229 A | 7/1975 | Taylor | |
| 4,013,069 A | 3/1977 | Hasty | |
| 4,321,929 A | 3/1982 | Lemelson | |
| 4,326,416 A | 4/1982 | Fredberg | |
| 4,469,099 A | 9/1984 | McEwen | |
| 4,479,494 A | 10/1984 | McEwen | |
| 4,520,819 A | 6/1985 | Birmingham | |
| 4,605,010 A | 8/1986 | McEwen | |
| 4,635,635 A | 1/1987 | Robinette-Lehman | |
| 4,671,290 A | 6/1987 | Miller | |
| D302,301 S | 7/1989 | Robinette-Lehman | |
| 5,193,549 A | 3/1993 | Bellin | |
| 5,201,758 A | 4/1993 | Glover | |
| 5,254,087 A | 10/1993 | McEwen | |
| 5,312,431 A | 5/1994 | McEwen | |
| 5,316,002 A | 5/1994 | Jackson | |
| 5,411,518 A | 5/1995 | Goldstein | |
| 5,413,582 A | 5/1995 | Eaton | |
| 5,439,477 A | 8/1995 | McEwen | |
| 5,445,144 A | 8/1995 | Wodicka | |
| 5,454,831 A | 10/1995 | McEwen | |
| 5,502,902 A | 4/1996 | Sussmann | |
| 5,556,415 A | 9/1996 | McEwen | |
| 5,575,762 A | 11/1996 | Peeler | |
| 5,584,853 A | 12/1996 | McEwen | |
| 5,607,447 A | 3/1997 | McEwen | |
| 5,649,954 A * | 7/1997 | McEwen | A61B 17/135 600/490 |
| 5,681,339 A | 10/1997 | McEwen | |
| 5,733,304 A * | 3/1998 | Spence | A61B 17/135 606/203 |
| 5,741,295 A | 4/1998 | McEwen | |
| 5,855,589 A | 1/1999 | McEwen et al. | |
| 5,911,735 A | 6/1999 | McEwen | |
| 5,931,853 A | 8/1999 | McEwen | |
| 5,935,146 A | 8/1999 | McEwen | |
| 5,968,073 A | 10/1999 | Jacobs | |
| 6,051,016 A | 4/2000 | Mesaros | |
| 6,149,600 A | 11/2000 | Poorman-Ketchum | |
| 6,210,423 B1 | 4/2001 | Simil | |
| 6,299,629 B1 | 10/2001 | Gruenfeld et al. | |
| 6,475,228 B1 | 11/2002 | Mesaros | |
| 6,484,371 B1 | 11/2002 | Romanko et al. | |
| 6,506,206 B1 | 1/2003 | Guzman | |
| 6,589,267 B1 | 7/2003 | Hui | |
| 6,605,103 B2 | 8/2003 | Hovanes | |
| 6,682,547 B2 | 1/2004 | McEwen et al. | |
| 7,479,154 B2 | 1/2009 | McEwen et al. | |
| 7,732,046 B2 | 6/2010 | LaBrosse et al. | |
| 7,758,607 B2 | 7/2010 | McEwen et al. | |
| 7,955,352 B2 | 6/2011 | McEwen et al. | |
| 8,137,378 B2 | 3/2012 | McEwen et al. | |
| 8,480,842 B2 | 7/2013 | McEwen et al. | |
| 9,011,483 B2 | 4/2015 | McEwen et al. | |
| 2003/0036771 A1 | 2/2003 | McEwen | |
| 2003/0167070 A1 | 9/2003 | McEwen | |
| 2004/0147956 A1 | 7/2004 | Hovanes | |
| 2004/0210167 A1 * | 10/2004 | Webster | A61B 17/00 601/1 |
| 2006/0054526 A1 * | 3/2006 | Dean | A61L 2/07 206/459.1 |
| 2006/0207144 A1 * | 9/2006 | Milliorn | G09F 3/10 40/637 |
| 2006/0287672 A1 | 12/2006 | McEwen et al. | |
| 2007/0032819 A1 | 2/2007 | McEwen et al. | |
| 2007/0219580 A1 | 9/2007 | McEwen et al. | |
| 2009/0266289 A1 | 10/2009 | Greene et al. | |
| 2013/0289612 A1 | 10/2013 | McEwen et al. | |

OTHER PUBLICATIONS

Bussani et al., "Improved Tacking of Limb Occlusion Pressure for Surgical Tourniquet," *IEEE Transaction on Biomedical Engineering*, vol. 34, No. 4, pp. 221-229 (Apr. 1988).

EP Supplementary Search Report in Corresponding Application No. EP07710741 (dated Feb. 27, 2012).

McEwen et al., "An adaptive Tourniquet for Improved Safety in Surgery," *IEEE Transactions on Biomedical Engineering*, vol. 29, No. 2, pp. 122-128 (Feb. 1982).

Younger et al., "Wide Contoured Thigh Cuffs and Automated Limb Occlusion Measurement Allow Lower Tourniquet Pressures," *Clinical Orthopedics and Related Research*, No. 428, pp. 286-293 (Nov. 2005).

* cited by examiner

METHOD AND APPARATUS FOR SHIELDING ENGAGEMENT OF A TOURNIQUET CUFF

CROSS REFERENCE TO RELATED APPLICATION

This is a continuation of U.S. patent application Ser. No. 15/853,336, filed Dec. 22, 2017, which is a continuation-in-part of U.S. patent application Ser. No. 13/932,093, filed Jul. 1, 2013, which is a continuation of U.S. patent application Ser. No. 12/828,078, filed Jun. 30, 2010 (now U.S. Pat. No. 8,480,842), which is a continuation of U.S. patent application Ser. No. 11/384,695, filed Mar. 20, 2006 (now U.S. Pat. No. 7,758,607), all of which are hereby incorporated by reference in their entirety.

FIELD

This invention pertains to pneumatic tourniquet cuffs commonly used for stopping arterial blood flow into a portion of a surgical patient's limb to facilitate the performance of a surgical procedure, and for facilitating intravenous regional anesthesia.

BACKGROUND

Typical surgical tourniquet systems of the prior art include a tourniquet cuff which encircles the limb of a surgical patient and a tourniquet instrument which is releasably connected to an inflatable bladder within the tourniquet cuff through a length of tubing, thereby establishing a gas-tight passageway between the cuff and the tourniquet instrument. The tourniquet instrument contains a pressurized gas source which is used to inflate and regulate the pressure in the tourniquet cuff above a minimum pressure required to stop arterial blood flow distal to the cuff, for a duration suitably long for the performance of a surgical procedure. Many types of surgical tourniquet systems have been described in the prior art, such as those described by McEwen in U.S. Pat. Nos. 4,469,099, 4,479,494, 5,439,477 and McEwen and Jameson in U.S. Pat. Nos. 5,556,415 and 5,855,589.

Standard cylindrical tourniquet cuffs are ideally suited for application to patients with cylindrical limbs. However, when applied to a patient with a tapered limb, a cylindrical cuff will not optimally match the limb taper, and will typically result in a snug fit proximally and a loose fit distally. Consequently, a cylindrical cuff may prove unable to achieve a bloodless field distal to the cuff at normal pressures or may require a substantially higher and more hazardous inflation pressure to achieve a bloodless field, and when inflated may have a tendency to roll or slide distally on the limb during a surgical procedure. In an effort to match the taper of a patient's limb at a desired cuff location, some tourniquet cuffs of the prior art are designed to have an arcuate shape, and are commonly called contour cuffs. When a contour cuff surrounds a limb having a matching taper, a uniformly snug fit can be achieved between the cuff and the limb from the proximal to distal cuff edges. Wide contour tourniquet cuffs of the prior art have been shown in the surgical literature to substantially reduce pressures required to create a bloodless surgical field distal to the inflated cuff (Younger et al., 'Wide Contoured Thigh Cuffs and Automated Limb Occlusion Measurement Allow Lower Tourniquet Pressures', Clin Orthop 428:286-293, 2004). Lower tourniquet pressures are associated in the surgical literature with lower risk of injuries to surgical patients.

Examples of contour cuffs of the prior art are described by Robinette-Lehman in U.S. Pat. No. 4,635,635, and in commercial products manufactured in accordance with its teachings ('Banana Cuff' sterile disposable tourniquet cuffs, Zimmer Arthroscopy Systems, Englewood CO). Cuffs described by Robinette-Lehman have an arcuate shape (defined by the distal radius), contain a single fastening system with fixed orientation, and include a rigid plastic stiffener. The cuff described in the '635 patent matches only a single limb taper for each particular cuff radius. For a limb with a differing taper, a cuff with a different arcuate shape matching that taper must be selected. When the cuff described by Robinette-Lehman '635 is applied to a limb with a differing taper, the overlapping proximal and distal edges of the cuff will not be superimposed upon one another, and will instead need to be skewed to obtain a sufficiently snug application and maximize the contact area between the cuff and the limb. The thick laminate construction and rigid stiffener included by Robinette-Lehman makes skewing the respective overlapping ends of the cuff difficult, and when skewed the orientation of the fixed fastening system may not be appropriate to safely and effectively allow the complete engagement of the hook and loop-type fastener (hereafter, such fastener being referred to as "VELCRO®") to secure the cuff on the limb when inflated.

Other contour cuffs of the prior art as described by McEwen in U.S. Pat. Nos. 5,312,431, 5,454,831, 5,578,055, 5,649,954, and 5,741,295. McEwen '431 describes a cuff with an arcuate shape which overcomes the limitations noted above, by replacing the rigid stiffener with fluted welds in the bladder, and by including a complex pivoting means for securing the cuff around a limb having any one of a wide range of limb tapers at the cuff location. Although the cuff described by McEwen '431 provides increased safety and improved shape-matching over a wide range of limb tapers, it does so by including a number of expensive components and laminated materials, with subassemblies that are labor-intensive and time-consuming to manufacture. As a result, the contour cuff of McEwen '431 has a high cost of manufacture, preventing its cost-effective use as sterile disposable tourniquet cuff for single surgical procedures.

The prior-art contour cuff described in McEwen '431 employs multiple pivoting VELCRO® hook fastening straps attached to D-shaped rings so that they may pivot when the cuff is wrapped around a tapered limb, and align with corresponding VELCRO® loop material fastened to the surface of the cuff. These D-shaped ring assemblies are in turn attached near one end of the cuff. The ring assemblies allow the straps to pivot over a predetermined range when the cuff is wrapped around the limb to fully engage with the corresponding loop material on the outer surface of the cuff. Manufacturing the ring assemblies described in McEwen '431 requires relatively large amounts of different materials, and requires numerous labor-intensive steps including cutting, alignment, sewing and welding, all of which must be completed by skilled operators.

There is a need for a contour cuff for surgical tourniquet systems that overcomes the hazards, problems and limitations of performance associated with prior-art contour cuffs, and that can be manufactured at a cost that is substantially lower than prior-art contour cuffs.

DETAILED DESCRIPTION

Figure 2:
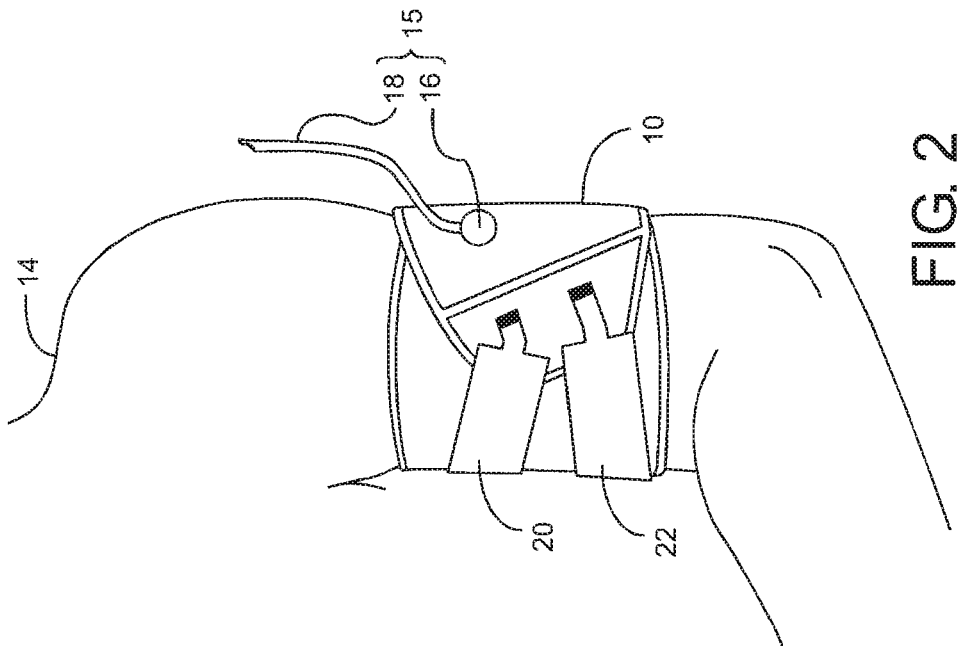
FIG. 2 is a view of the preferred embodiment applied to a cylindrically shaped patient
Figure 1:
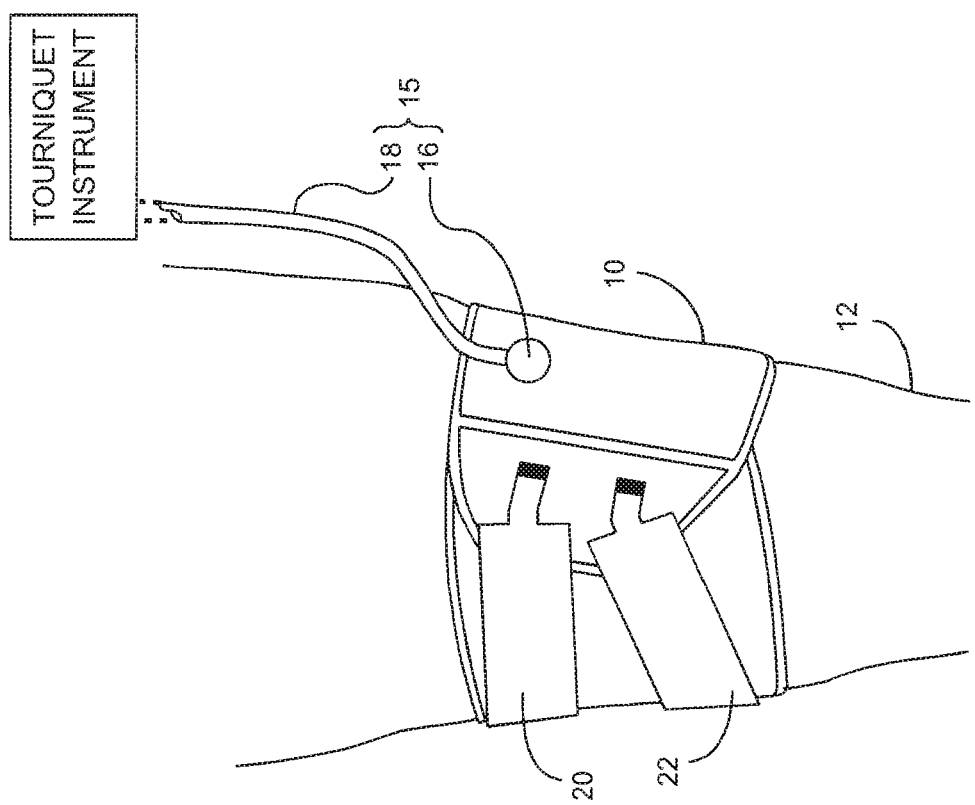
FIG. 1 is a view of the preferred embodiment applied to a tapered patient limb.

FIG. 1 shows the preferred embodiment in a surgical application and depicts contour tourniquet cuff 10 secured circumferentially around a tapered patient limb 12. FIG. 2 depicts contour cuff 10 secured circumferentially around a substantially cylindrically shaped patient limb 14.

Referring to FIG. 1, the inflatable portion of contour tourniquet cuff 10 completely encircles patient limb 12 and is inflated by a source of pressurized gas to a pressure that will occlude the flow of arterial blood in patient limb 12 distal to cuff 10. Cuff port 15 is comprised of port inlet 16 and tubing 18 and provides a gas tight pneumatic passageway to the inflatable portion of cuff 10. Tubing 18 is made from flexible thermoplastic tubing and is permanently bonded to port inlet 16. Tubing 18 is fitted with a suitable connector (not shown) to permit attachment to a tourniquet instrument such as that described by McEwen et al. in U.S. patent application Ser. No. 11/122,600, for the inflation of cuff 10. Tubing 18 has a length at least equal to the maximum width of cuff 10 and allows cuff 10 to be used inside a sterile surgical field. In the preferred embodiment shown, cuff 10 is a single port cuff, where cuff port 15 provides a single pneumatic passageway to the inflatable portion of cuff 10. Those skilled in the art will appreciate that the features described in the preferred embodiment may also be applied to tourniquet cuffs having more than one port, such as those described by U.S. Pat. Nos. 4,469,099, 4,479,494, and 5,254,087.

Figure 3:
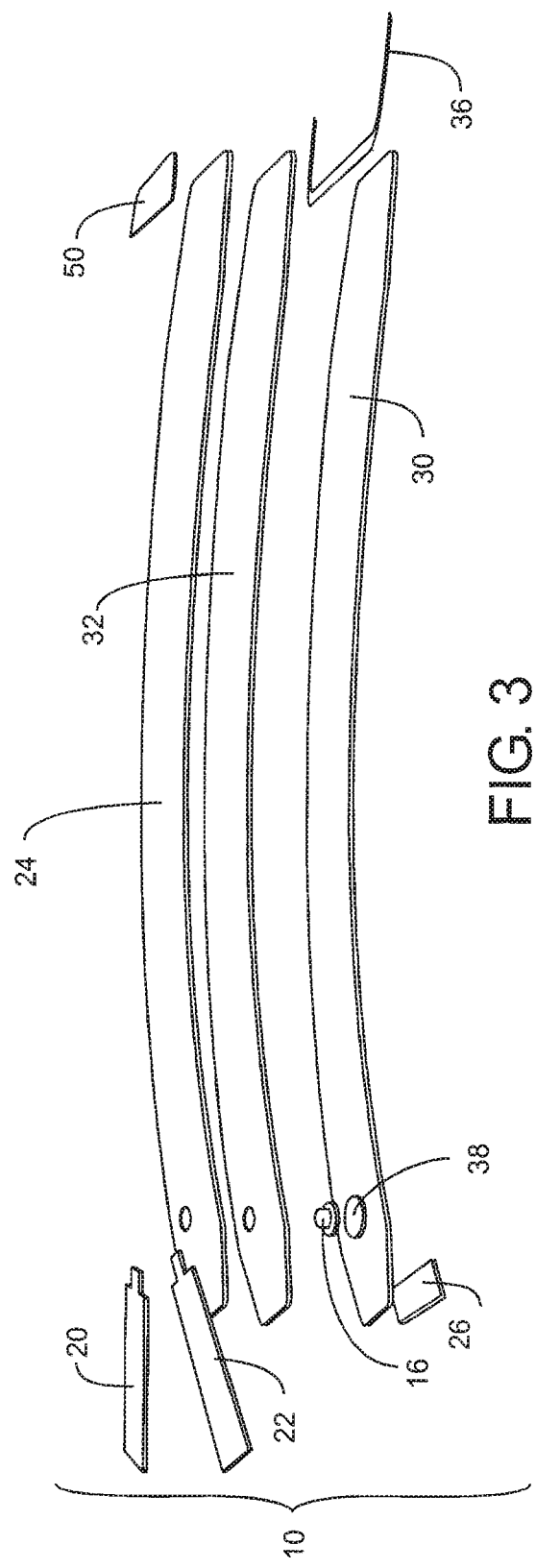
FIG. 3 is an exploded view of the preferred embodiment.
Figure 4:
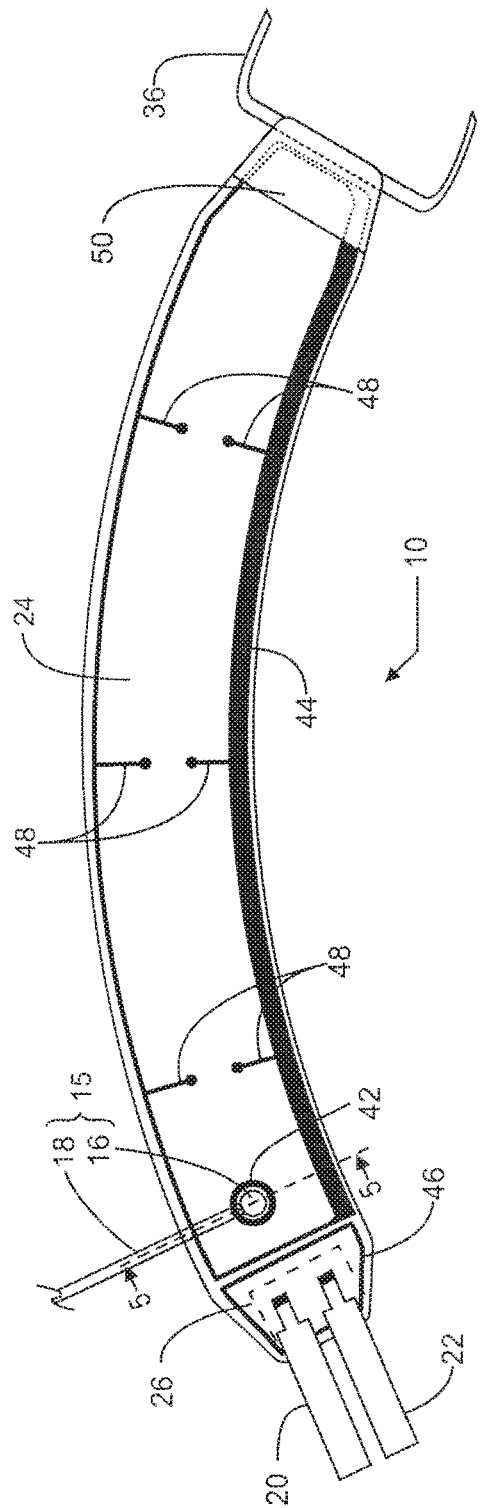
FIG. 4 is a top view of the preferred embodiment.

As shown in FIGS. 3 and 4, cuff 10 has a substantially arcuate shape with the width of the cuff reduced near the end edges. The arcuate shape of cuff 10 and the degree to which the width near the end edges is reduced are predetermined to allow cuff 10 to be applied to limbs with a predetermined range of tapers such that cuff 10 remains substantially in contact with the limb along its width around the circumference of the limb. When cuff 10 is correctly applied to a patient limb as shown in FIGS. 1 and 2, the side edge of cuff 10 with the greater radius is proximal and the side edge with the lesser radius is distal on the limb.

As shown in FIGS. 1 and 2, cuff 10 is secured around the limb by securing straps 20 and 22. Securing straps 20 and 22 are non-releasably attached to a non-inflating region of cuff 10 near an end edge. Securing straps 20 and 22 have fastening portions which releasably engage with the outer surface of cuff 10 and bending portions which permit the fastening portions to be positioned such that they can completely engage the outer surface within the side edges of cuff 10. In the preferred embodiment the outer surface of cuff 10 and the fastening portions of securing straps 20 and 22 are formed from VELCRO® materials. The outer surface of cuff 10 is a loop type material and the fastening portions of securing straps 20 and 22 are formed from hook type material.

Limb 14 shown in FIG. 2, has a substantially cylindrical shape and has been selected to represent a limb with the minimum amount of taper to which cuff 10 can be applied. As shown in FIG. 2, the bending portions of securing straps 20 and 22 twist to permit the fastening portions to move towards the proximal side edge of the cuff so that they may completely engage the outer surface of cuff 10 and maintain their substantially flat shape.

Limb 12 shown in FIG. 1 has a substantially tapered shape and has been selected to represent a limb with the maximum amount of taper to which cuff 10 can be applied. As shown in FIG. 1, the bending portions of securing straps 20 and 22 twist to permit the fastening portions to move towards the distal side edge of the cuff so that they may completely engage the outer surface of cuff 10.

When cuff 10 is properly secured around a limb the fastening portions of securing straps 20 and 22 are completely engaged within the side edges of the cuff. The materials comprising the outer surface of cuff 10 and the fastening portions of securing straps 20 and 22 have contrasting colors. In the preferred embodiment, the outer surface of cuff 10 is colored black and the fastening portions of securing straps 20 and 22 are colored white. The contrasting colors provide a user of cuff 10 with a visual indication that the securing straps have been correctly positioned within the side edges of the cuff. When the securing straps are correctly positioned the outer surface of the cuff will be clearly visible completely around the perimeter of the ends of the securing straps.

As described below, cuff 10 is constructed of materials that are appropriate for a single use sterile disposable tourniquet cuff. To permit cuff 10 to be used in a sterile surgical field, cuff 10 is sterilized at time of manufacture by exposure to a sterilizing agent within a sterilizing process determined to be safe and effective. To prevent deterioration of the cuff, and to maintain the integrity of the pneumatic passageways within cuff 10, a sterilization agent and process that will not harm the materials or components of cuff 10 is selected by the manufacturer. In the preferred embodiment cuff 10 is sterilized by exposure to gamma radiation or electron beam radiation.

The cost of materials and labor are important considerations in the manufacture of tourniquet cuffs intended for a single use and then disposal. To minimize the cost of materials and assembly of cuff 10, materials are selected which are not intended to withstand exposure to subsequent sterilization and cleaning processes. The subsequent sterilization or cleaning of cuff 10 by agents and processes commonly used in health care facilities, such as ethylene oxide gas sterilization, hydrogen peroxide gas sterilization, high temperature and pressure steam sterilization, sterilization by other chemical agents, and pasteurization, are all capable of adversely affecting the integrity of the materials and pneumatic passageways of cuff 10.

FIG. 3 is an exploded view of the individual components that are joined together as described below to form cuff 10. For clarity, cuff tubing 18 is not shown in FIG. 3.

To reduce manufacturing equipment and labor costs it is desirable to manufacture cuff 10 in a single dielectric welding operation. This requires that the thermoplastic polymers comprising the components of cuff 10 be prevented from welding at selected surfaces as described below.

Top sheet 24 forms the outer surface of cuff 10 and is a flexible knit loop nylon material (for example, 200 Series Loop Material, Aplix Inc., Charlotte, N.C. 28241) adapted for secure engagement with the hook material of the fastening portions of securing straps 20 and 22 and secondary fastener 26. It will be appreciated that top sheet 24 may be made from other types of flexible sheet materials to which VELCRO® materials have been permanently attached and that the sheet material may not be completely covered by the VELCRO® material. For example top sheet 24 may be comprised of a woven nylon fabric with nylon loop material bonded to the fabric only in predetermined areas for engagement with the fastening portions of securing straps 20 and 22.

Securing straps 20 and 22 are formed from substantially flat flexible inextensible materials, such as the nylon hook material that is commonly used in hook and loop VEL-CRO® fastening applications. As described above, securing straps 20 and 22 have a fastening portion and a bending portion. The bending portion of securing strap 20 and 22 has a width less than the width of the fastening portion, the reduced width of the bending portion allows the bending portion to twist out of its substantially flat shape to facilitate positioning of the fastening portion. It will be appreciated that the fastening portion and bending portion of securing straps 20 and 22 may be comprised of different materials that are permanently joined together to form the securing strap, for example the bending portion may be comprised of a material that is substantially more flexible than the material comprising the fastening portion. For further example, securing straps 20 and 22 could be comprised of a bending portion formed from a segment of grosgrain ribbon which is permanently joined to a fastening portion formed from a segment of nylon hook material. As described above the material comprising the fastening portion of securing straps 20 and 22 is a contrasting color to the material comprising top sheet 24.

Secondary fastener 26 is comprised of hook material similar to the hook material that forms the fastening portions of securing straps 20 and 22. Secondary fastener 26 is attached to the outer surface of bottom sheet 30 and engages with the loop material of top sheet 24. Secondary fastener 26 facilitates cuff application and alignment by providing a means for maintaining cuff 10 in position around patient limb 12 while securing straps 20 and 22 are positioned and engaged. The additional fastening surface area provided by secondary fastener 26 allows the length of securing straps to be reduced from what otherwise would be required to maintain cuff 10 secured around a limb and thereby increases the range of limb tapers to which cuff 10 can be applied. Secondary fastener 26 also helps improve the stability of cuff 10 on the limb by resisting lateral movement of the overlapped cuff end.

Bottom sheet 30 and middle sheet 32 are made of a flexible woven nylon cloth, coated on one surface with a thermoplastic polymer (for example, 70 Denier nylon cloth coated with thermoplastic polyurethane 0.004" thick). The thermoplastic polymer coating prevents the passage of gas through bottom sheet 30 and middle sheet 32 and allows bottom sheet 30 to be welded to middle sheet 32 in selected areas to form an inflatable bladder 34 as shown in cross-section in FIG. 5. In the preferred embodiment the thermoplastic coating on bottom sheet 30 and middle sheet 32 is polyurethane, but it will be appreciated by those skilled in the art that other thermoplastic polymers may be used as coatings on bottom sheet 30 and middle sheet 32 providing they can be joined with sufficient strength to maintain the integrity of cuff 10 when inflated.

Tie strap 36 is a soft fabric polymer coated ribbon material (Grosgrain ⅝" wide, Dynatex Textiles Inc., Toronto, Ontario, Canada) that is shown in FIG. 3 positioned between middle sheet 32 and bottom sheet 30 at an end edge of cuff 10. Tie strap 36 is secured to bottom sheet 30 and middle sheet 32 by welds and provides a means for the user to align and pull cuff 10 snug around the limb. When cuff 10 has been secured around a limb the ends of tie strap 36 are tied together to help maintain the overlapping portion of the cuff in alignment around the limb by preventing the cuff from twisting, telescoping and rolling on the limb when inflated. It will be apparent that tie strap 36 may also be positioned between top sheet 24 and middle sheet 32 near an end edge of cuff 10 and secured by stitching at the side edges of cuff 10.

Figure 5:
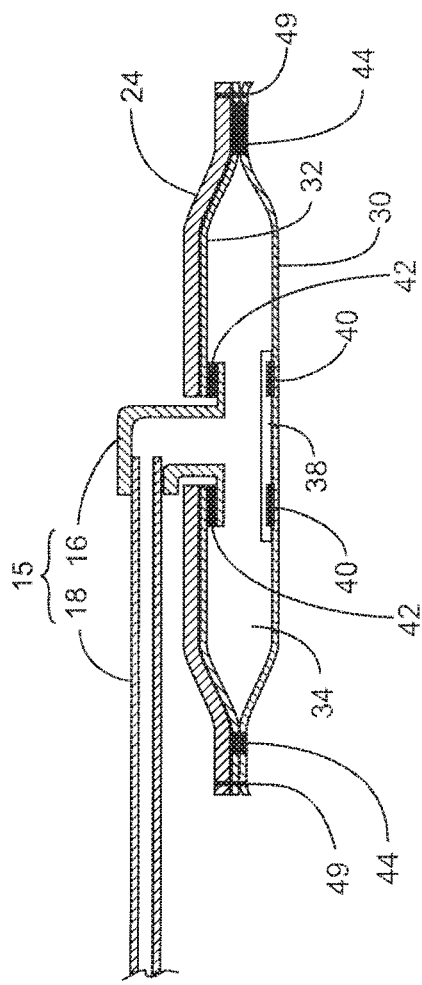
FIG. 5 is a section view taken from FIG. 4.

As shown in FIG. 4 and in cross-section in FIG. 5, port inlet 16 has a right angle configuration and has a flange for bonding with middle sheet 32. Port inlet 16 is made of a thermoplastic polymer that is compatible with and can be welded to the thermoplastic coating of middle sheet 32 to form a gas-tight seal.

Port mask 38 is interposed between port inlet 16 and bottom sheet 30. In the preferred embodiment, port mask 38 is formed from the same material as bottom sheet 30.

To permit the cost effective manufacture of cuff 10 it is desirable to form the welds joining middle sheet 32 to bottom sheet 30 and port inlet 16 in a single dielectric welding operation. To prevent port inlet 16 from bonding to bottom sheet 30 during the dielectric welding operation port mask 38 is placed below port inlet 16 such that the polyurethane coated surface of port mask 38 is facing the polyurethane surface of bottom sheet 30 and the nylon cloth surface is facing port inlet 16.

During the welding operation, port mask 38 bonds to bottom sheet 30 in the region of the weld area joining the flange of port inlet 16 to middle sheet 32 and forms port mask weld 40 as shown in the cross-section of cuff 10 depicted in FIG. 5. Port mask weld 40 secures port mask 38 within inflatable bladder 34 preventing it from interfering with the inflation and deflation of inflatable bladder 34. The nylon fabric surface of port mask 38 is not compatible with the material comprising port inlet 16 and thereby prevents port inlet 16 from bonding to the top surface of port mask 38 during the welding operation.

FIG. 4 is a top view of the preferred embodiment laid flat and shows the areas where middle sheet 32 is welded to bottom sheet 30 and port inlet 16. Port inlet 16 is welded to middle sheet 32 at port weld 42. Middle sheet 32 is also welded to bottom sheet 30 at bladder perimeter weld 44, non-inflating region weld 46, and flute welds 48. Top sheet 24 is secured to middle sheet 32 and bottom sheet 30 by stitching 49 around the perimeter of top sheet 24 as shown in FIG. 5.

Bladder perimeter weld 44 defines inflatable bladder 34 of cuff 10 which is shown in cross-section in FIG. 5. Bladder 34 has distal and proximal side edges; the proximal side edge of bladder 34 has a greater radius than the distal side edge of bladder 34. In the preferred embodiment bladder perimeter weld 44 has a greater width along the distal side edge of bladder 34 than it has along the proximal side edge of bladder 34. The increased width of the bladder perimeter weld along the distal edge of bladder 34 acts to stiffen the edge of the cuff and thereby help improve the cuffs roll stability when inflated. Only the width of the bladder weld along the distal edge is increased as inflated cuffs tend to roll only distally down the limb. By increasing the width of the bladder weld only along one side edge in the preferred embodiment the width of the inflatable bladder is maximized for a given overall cuff width. Prior art cylindrical cuffs that are substantially rectangular in shape do not have defined proximal and distal side edges; their orientation when applied to a limb is not predetermined by their shape. Wide bladder welds in prior art cuffs to improve stability must be made along both side edges of the bladder as the cuff may be applied in either orientation, thereby reducing the maximum possible bladder width for a given cuff width.

Middle sheet 32 and bottom sheet 30 are joined together by several flute welds 48; these welds are perpendicular to the side edges of cuff 10 and extend radially towards the centerline of cuff 10. Flute welds 48 act in place of a stiffing element to constrain inflatable bladder 34 of cuff 10 when inflated. Flute welds 48 prevent relative lateral movement between selected areas of bottom sheet 30 and top sheet 24 reducing the tendency of cuff 10 to roll along the longitudinal axis of the limb.

The perimeter of non-inflating region weld 46 shown in FIG. 4, defines a non-inflating region near an end edge of cuff 10. Secondary fastener 26 is attached to the outer surface of bottom sheet 30 by stitching around its perimeter within the non-inflating region. Securing straps 20 and 22 are attached to the outer surface of top sheet 24 within the non-inflating region also by stitching. The stitching attaching securing straps 20 and 22 passes through the material of secondary fastener 26 which helps to distribute the loads at the attachment points of securing straps 20 and 22 across the end edge of cuff 10.

As shown in FIG. 4, securing straps 20 and 22 are attached near the bending portion to the outer surface of top sheet 24 such that they are substantially parallel to the center line of cuff 10. Securing strap 20 is attached between the centerline and the proximal side edge of the cuff. Securing strap 22 is attached between the centerline and the distal side edge of the cuff. As described above the bending portions of securing straps 20 and 22 allow the fastening portions to be placed in positions other than those substantially parallel to the center line of cuff 10.

It will be apparent that securing straps 20 and 22, and secondary fastener 26 may be attached by other mechanical fastening means or by welding or adhesives. It will also be apparent that bladder 34 could be extended eliminating non-inflating region weld 46 and the non-inflating region of the cuff.

Cuff 10 includes a label 50, shown in FIGS. 3 and 4. Label 50 has printed marks to indicate to a user of cuff 10: that cuff 10 is intended for a single use; the proximal and distal side edges of cuff 10; the area of top sheet 24 that secondary fastener 26 and securing straps 20 and 22 are to be completely engaged with. Label 50 is comprised of printed Tyvek label material with a thermally activated adhesive backing. Label 50 is die cut to match the shape of cuff 10 near an end edge and adhered to top sheet 24 near an end edge as shown in FIGS. 3 and 4. The Tyvek material of label 50 does not engage with the hook materials of secondary fastener 26 and securing straps 20 and 22. Label 50 acts as an engagement barrier, preventing secondary fastener 26 and securing straps 20 and 22 from engaging with the loop material of top sheet 24 in the region covered by label 50. To insure that inflatable bladder 34 completely encircles a limb when secondary fastener 26 and securing straps 20 and 22 are completely engaged with top sheet 24, the length of label 50 is selected in the preferred embodiment to be substantially equivalent to or greater than the length of the non-inflating region of cuff 10 to which securing straps 20 and 22 and secondary fastener 26 are fixed.

Label 50 also acts to stiffen the end edge of cuff 10 and helps prevent the end edge from curling as cuff 10 is pulled snug around a limb by tension on tie strap 36.

For safety, label 50 may also provide a visible indication of contact with fluid such as blood, surgical prep solutions, or cleaning agents, for example by discoloration. Label 50 may be designed to absorb fluid and deteriorate after use. Physical deterioration of label 50 reduces the effectiveness of label 50 as an engagement barrier and provide an indication to the user that cuff 10 has been used and/or contaminated, thereby further improving the safety and effectiveness of cuff 10 as a single-use cuff not intended for cleaning and reuse. It will be apparent that label 50 may be made with other low-cost materials such as printed cellulose-based paper material, and may be attached to the top sheet 24 through other methods such as sewing, adhesives or welding.

The preferred embodiment is substantially comprised of top sheet 24, middle sheet 32 and bottom sheet 30. It will be apparent that top sheet 24 may be coated with a thermoplastic coating compatible with the coating on bottom sheet 30 and that middle sheet 32 may be eliminated and an inflatable bladder formed between top sheet 24 and bottom sheet 30. This would also eliminate the need for stitching 49 securing top sheet 24 to middle sheet 32 and bottom sheet 30.

In the preferred embodiment flute welds 48 help improve the roll stability of cuff 10 when inflated on a limb by preventing middle sheet 32 from moving laterally with respect to bottom sheet 30 at selected locations. It will be apparent that flute welds 48 could be replaced by other means to help prevent roll, such as a stiffening sheet made from a thermoplastic material less flexible than middle sheet 32 and having an arcuate shape. A stiffening sheet may be interposed between top sheet 24 and middle sheet 32 or be interposed between middle sheet 32 and bottom sheet 30 within the perimeter of inflatable bladder 34. To further improve stability, the stiffening sheet may be bonded to the inner surface of middle sheet 32 such as described in U.S. patent application Ser. No. 11/304,363.

The embodiment illustrated is not intended to be exhaustive or limit the invention to the precise form disclosed. It is chosen and described in order to explain the principles of the invention and its application and practical use, and thereby enable others skilled in the art to utilize the invention.

We claim:

1. A tourniquet cuff apparatus, comprising:
    an inner sheet joined to an outer sheet to form an inflatable cuff, the cuff having opposing ends, and distal and proximal side edges extending between the opposing ends, the outer sheet extending from a first end of the cuff to an opposing second end and comprising material having an outer fastening surface that includes a first fastener component;
    an elongated, securing strap attached near the first end of the cuff, formed to curve around and conform to the shape of a limb to which the cuff is applied, the strap including a second fastener component that can releasably engage the outer fastening surface thereby to enable engagement of the second fastener component on the strap with the outer fastening surface between the distal and proximal side edges of the cuff; and
    an engagement barrier having a shape matched to the second end of the cuff, adhered to and covering a region of the outer fastening surface extending from the distal side edge to the proximal side edge near the second end of the cuff and operable to prevent engagement of the securing strap to the first fastener component within the region of the outer fastening surface covered by the engagement barrier.

2. The apparatus in claim 1 wherein the engagement barrier provides a visible indication of contact with a fluid.

3. The apparatus of claim 2 wherein the visible indication comprises a color change.

4. The apparatus of claim 2 wherein the fluid comprises blood.

5. The apparatus of claim 2 wherein the fluid comprises a liquid employed to clean the cuff after usage.

6. The apparatus of claim 2 wherein the visible indication is a physical deterioration of the engagement barrier.

7. The apparatus of claim 6 wherein the physical deterioration renders the engagement barrier inoperable within the region.

8. A method of shielding engagement of a tourniquet cuff, comprising:
provFiding or obtaining a tourniquet cuff, the tourniquet cuff comprising:
an inner sheet joined to an outer sheet to form an inflatable cuff, the cuff having opposing ends, and distal and proximal side edges extending between the opposing ends, the outer sheet extending from a first end of the cuff to an opposing second end and comprising material having an outer fastening surface that includes a first fastener component; and
an elongated, securing strap attached near the first end of the cuff, formed to curve around and conform to a shape of a limb to which the cuff is applied, the strap including a second fastener component that can releasably engage the outer fastening surface thereby to enable engagement of the second fastener component on the strap with the outer fastening surface between the distal and proximal side edges of the cuff; and
applying an engagement barrier having a shape matched to the second end of the cuff, adhered to and covering a region of the outer fastening surface extending from the distal side edge to the proximal side edge near the second end of the cuff and operable to prevent engagement of the securing strap to the first fastener component within the region of the outer fastening surface covered by the engagement barrier.

9. The method of claim 8, further comprising determining whether the engagement barrier may be ineffective in preventing engagement within the region.

10. The method of claim 8, further comprising visually inspecting the engagement barrier to determine if the engagement barrier has a visual appearance indicating that the engagement barrier may be ineffective in preventing engagement within the region.

11. The method of claim 8, wherein the engagement barrier is comprised of a cellulose-based paper material.

\* \* \* \* \*